(12) United States Patent
Reggiardo et al.

(10) Patent No.: US 8,471,714 B2
(45) Date of Patent: *Jun. 25, 2013

(54) METHOD AND SYSTEM FOR PROVIDING DATA MANAGEMENT IN DATA MONITORING SYSTEM

(75) Inventors: Christopher V. Reggiardo, Castro Valley, CA (US); Mark K. Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/341,853

(22) Filed: Dec. 30, 2011

(65) Prior Publication Data

US 2012/0101353 A1    Apr. 26, 2012

Related U.S. Application Data

(63) Continuation of application No. 13/022,610, filed on Feb. 7, 2011, now Pat. No. 8,089,363, which is a continuation of application No. 12/849,007, filed on Aug. 2, 2010, now Pat. No. 7,884,729, which is a continuation of application No. 11/383,945, filed on May 17, 2006, now Pat. No. 7,768,408.

(60) Provisional application No. 60/681,942, filed on May 17, 2005.

(51) Int. Cl.
*G08B 23/00* (2006.01)

(52) U.S. Cl.
USPC ............... 340/573.1; 340/539.12; 600/365

(58) Field of Classification Search
USPC ........................................ 340/573.1
See application file for complete search history.

(56) References Cited

U.S. PATENT DOCUMENTS

| | | | |
|---|---|---|---|
| 2,915,579 A | 12/1959 | Mendelsohn | |
| 3,374,337 A | 3/1968 | Burley | |
| 3,510,747 A | 5/1970 | Petrides | |
| 3,541,892 A | 11/1970 | Kubinek et al. | |
| 3,606,592 A | 9/1971 | Madurski et al. | |
| 3,750,687 A | 8/1973 | Williams | |
| 3,843,455 A | 10/1974 | Bier | |
| 3,923,060 A | 12/1975 | Elinwood | |
| 3,930,493 A | 1/1976 | Williamson | |

(Continued)

FOREIGN PATENT DOCUMENTS

| | | |
|---|---|---|
| CA | 2143172 | 7/2005 |
| CA | 2413148 | 8/2010 |

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Kerri McNally
(74) *Attorney, Agent, or Firm* — Jackson & Co., LLP

(57) ABSTRACT

Method and system for providing a fault tolerant data receiver unit configured with a partitioned or separate processing units, each configured to perform a predetermined and/or specific processing associated with the one or more substantially non-overlapping functions of the data monitoring and management system is provided.

19 Claims, 3 Drawing Sheets

U.S. PATENT DOCUMENTS

| | | |
|---|---|---|
| 3,938,140 A | 2/1976 | Garcia et al. |
| 3,994,799 A | 11/1976 | Yao et al. |
| 4,018,547 A | 4/1977 | Rogen |
| 4,048,551 A | 9/1977 | Bosik |
| 4,121,282 A | 10/1978 | Ohsawa |
| 4,146,029 A | 3/1979 | Elinwood |
| 4,172,770 A | 10/1979 | Semersky et al. |
| 4,193,397 A | 3/1980 | Tucker et al. |
| 4,268,173 A | 5/1981 | Barnard et al. |
| 4,288,793 A | 9/1981 | Lotscher |
| 4,309,156 A | 1/1982 | Gonner et al. |
| 4,360,019 A | 11/1982 | Portner et al. |
| 4,362,052 A | 12/1982 | Heath et al. |
| 4,401,122 A | 8/1983 | Clark, Jr. |
| 4,439,197 A | 3/1984 | Honda et al. |
| 4,441,968 A | 4/1984 | Emmer et al. |
| 4,447,224 A | 5/1984 | DeCant, Jr. et al. |
| 4,458,686 A | 7/1984 | Clark, Jr. |
| 4,467,811 A | 8/1984 | Clark, Jr. |
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,655,880 A | 4/1987 | Liu |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,883,409 A | 11/1989 | Strohmeier et al. |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Busch et al. |
| 5,078,683 A | 1/1992 | Sancoff et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,264,104 A | 11/1993 | Gregg et al. |
| 5,267,026 A | 11/1993 | Kawahara et al. |
| 5,278,997 A | 1/1994 | Martin |
| 5,284,423 A | 2/1994 | Holdsworth et al. |
| 5,284,425 A | 2/1994 | Holtermann et al. |
| 5,291,614 A | 3/1994 | Baker et al. |
| 5,291,887 A | 3/1994 | Stanley et al. |
| 5,320,725 A | 6/1994 | Gregg et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,515,390 A | 5/1996 | Benton |
| 5,517,434 A | 5/1996 | Hanson et al. |
| 5,526,844 A | 6/1996 | Kamen et al. |
| 5,527,288 A | 6/1996 | Gross et al. |
| 5,532,686 A | 7/1996 | Urbas et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,573,506 A | 11/1996 | Vasko |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,620,579 A | 4/1997 | Genshaw et al. |
| 5,622,413 A | 4/1997 | Kim et al. |
| 5,622,482 A | 4/1997 | Lee |
| 5,634,468 A | 6/1997 | Platt et al. |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,665,222 A | 9/1997 | Heller et al. |
| 5,671,301 A | 9/1997 | Kuperschmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,724,030 A | 3/1998 | Urbas et al. |
| 5,738,220 A | 4/1998 | Geszler |
| 5,741,211 A | 4/1998 | Renirie et al. |
| 5,748,872 A | 5/1998 | Norman |
| 5,749,907 A | 5/1998 | Mann |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,804,047 A | 9/1998 | Karube et al. |
| 5,812,102 A | 9/1998 | Sprole et al. |
| 5,814,020 A | 9/1998 | Gross |
| 5,814,599 A | 9/1998 | Mitragotri et al. |
| 5,815,303 A | 9/1998 | Berlin |
| 5,822,715 A | 10/1998 | Worthington et al. |

| | | | | | | |
|---|---|---|---|---|---|---|
| 5,825,488 | A | 10/1998 | Kohl et al. | 6,157,442 A | 12/2000 | Raskas |
| 5,833,603 | A | 11/1998 | Kovacs et al. | 6,160,449 A | 12/2000 | Klomsdorf et al. |
| 5,848,990 | A | 12/1998 | Cirelli et al. | 6,162,202 A | 12/2000 | Sicurelli et al. |
| 5,851,197 | A | 12/1998 | Marano et al. | 6,162,611 A | 12/2000 | Heller et al. |
| 5,856,631 | A | 1/1999 | Julien | 6,164,284 A | 12/2000 | Schulman et al. |
| 5,858,001 | A | 1/1999 | Tsals et al. | 6,173,160 B1 | 1/2001 | Liimatainen |
| 5,873,026 | A | 2/1999 | Reames | 6,175,752 B1 | 1/2001 | Say et al. |
| 5,875,417 | A | 2/1999 | Golden | 6,180,416 B1 | 1/2001 | Kurnik et al. |
| 5,885,211 | A | 3/1999 | Eppstein et al. | 6,185,452 B1 | 2/2001 | Schulman et al. |
| 5,891,049 | A | 4/1999 | Cyrus et al. | 6,186,982 B1 | 2/2001 | Gross et al. |
| 5,899,855 | A | 5/1999 | Brown | 6,200,265 B1 | 3/2001 | Walsh et al. |
| 5,913,833 | A | 6/1999 | Elstrom et al. | 6,201,980 B1 | 3/2001 | Darrow et al. |
| 5,918,603 | A | 7/1999 | Brown | 6,203,288 B1 | 3/2001 | Kottke |
| 5,919,167 | A | 7/1999 | Mulhauser | 6,206,841 B1 | 3/2001 | Cunningham et al. |
| 5,923,512 | A | 7/1999 | Brownlow et al. | 6,208,894 B1 | 3/2001 | Schulman et al. |
| 5,931,814 | A | 8/1999 | Alex et al. | 6,212,416 B1 | 4/2001 | Ward et al. |
| 5,947,921 | A | 9/1999 | Johnson et al. | 6,215,206 B1 | 4/2001 | Chitayat |
| 5,948,512 | A | 9/1999 | Kubota et al. | 6,222,514 B1 | 4/2001 | DeLuca |
| 5,951,485 | A | 9/1999 | Cyrus et al. | 6,228,100 B1 | 5/2001 | Schraga |
| 5,951,582 | A | 9/1999 | Thorne et al. | 6,232,370 B1 | 5/2001 | Kubota et al. |
| 5,951,836 | A | 9/1999 | McAleer et al. | 6,233,471 B1 | 5/2001 | Berner et al. |
| 5,954,643 | A | 9/1999 | Van Antwerp et al. | 6,233,539 B1 | 5/2001 | Brown |
| 5,965,380 | A | 10/1999 | Heller et al. | 6,242,961 B1 | 6/2001 | Liu et al. |
| 5,968,011 | A | 10/1999 | Larsen et al. | 6,245,060 B1 | 6/2001 | Loomis et al. |
| 5,971,922 | A | 10/1999 | Arita et al. | 6,248,067 B1 | 6/2001 | Causey, III et al. |
| 5,972,199 | A | 10/1999 | Heller et al. | 6,262,708 B1 | 7/2001 | Chu |
| 5,993,411 | A | 11/1999 | Choi | 6,272,364 B1 | 8/2001 | Kurnik |
| 5,994,878 | A | 11/1999 | Ostergaard et al. | 6,278,425 B1 | 8/2001 | DeLuca |
| 5,997,501 | A | 12/1999 | Gross et al. | 6,280,587 B1 | 8/2001 | Matsumoto |
| 6,001,067 | A | 12/1999 | Shults et al. | 6,283,926 B1 | 9/2001 | Cunningham et al. |
| 6,002,961 | A | 12/1999 | Mitragotri et al. | 6,283,951 B1 | 9/2001 | Flaherty et al. |
| 6,011,486 | A | 1/2000 | Casey | 6,284,478 B1 | 9/2001 | Heller et al. |
| 6,014,577 | A | 1/2000 | Henning et al. | 6,288,653 B1 | 9/2001 | Shih |
| 6,017,328 | A | 1/2000 | Fischell et al. | 6,291,200 B1 | 9/2001 | LeJeune et al. |
| 6,018,678 | A | 1/2000 | Mitragotri et al. | 6,293,925 B1 | 9/2001 | Safabash et al. |
| 6,023,629 | A | 2/2000 | Tamada | 6,294,997 B1 | 9/2001 | Paratore et al. |
| 6,024,539 | A | 2/2000 | Blomquist et al. | 6,295,506 B1 | 9/2001 | Heinonen et al. |
| 6,026,320 | A | 2/2000 | Carlson et al. | 6,298,254 B2 | 10/2001 | Tamada |
| 6,027,459 | A | 2/2000 | Shain et al. | 6,298,255 B1 | 10/2001 | Cordero et al. |
| 6,027,496 | A | 2/2000 | Loomis et al. | 6,299,578 B1 | 10/2001 | Kurnik et al. |
| 6,027,692 | A | 2/2000 | Galen et al. | 6,301,499 B1 | 10/2001 | Carlson et al. |
| 6,032,059 | A | 2/2000 | Henning et al. | 6,306,104 B1 | 10/2001 | Cunningham et al. |
| 6,041,253 | A | 3/2000 | Kost et al. | 6,309,351 B1 | 10/2001 | Kurnik et al. |
| 6,041,665 | A | 3/2000 | Hussain | 6,312,888 B1 | 11/2001 | Wong et al. |
| 6,059,546 | A | 5/2000 | Brenan et al. | 6,315,721 B2 | 11/2001 | Schulman et al. |
| 6,063,039 | A | 5/2000 | Cunningham et al. | 6,326,160 B1 | 12/2001 | Dunn et al. |
| 6,064,368 | A | 5/2000 | Kang | 6,329,161 B1 | 12/2001 | Heller et al. |
| 6,066,243 | A | 5/2000 | Anderson et al. | 6,331,244 B1 | 12/2001 | Lewis et al. |
| 6,067,017 | A | 5/2000 | Stewart et al. | 6,338,790 B1 | 1/2002 | Feldman et al. |
| 6,067,463 | A | 5/2000 | Jeng et al. | 6,341,232 B1 | 1/2002 | Conn et al. |
| 6,071,249 | A | 6/2000 | Cunningham et al. | 6,356,776 B1 | 3/2002 | Berner et al. |
| 6,071,251 | A | 6/2000 | Cunningham et al. | 6,360,888 B1 | 3/2002 | McIvor et al. |
| 6,073,031 | A | 6/2000 | Helstab et al. | 6,366,793 B1 | 4/2002 | Bell et al. |
| 6,077,660 | A | 6/2000 | Wong et al. | 6,368,141 B1 | 4/2002 | VanAntwerp et al. |
| 6,081,104 | A | 6/2000 | Kern | 6,368,274 B1 | 4/2002 | Van Antwerp et al. |
| 6,082,289 | A | 7/2000 | Cavallaro | 6,372,371 B1 | 4/2002 | Iarochenko et al. |
| 6,083,710 | A | 7/2000 | Heller et al. | 6,375,344 B1 | 4/2002 | Hanson et al. |
| 6,085,871 | A | 7/2000 | Karamata | 6,375,638 B2 | 4/2002 | Nason et al. |
| 6,086,575 | A | 7/2000 | Mejslov | 6,377,894 B1 | 4/2002 | Deweese et al. |
| 6,091,975 | A | 7/2000 | Daddona et al. | 6,379,301 B1 | 4/2002 | Worthington et al. |
| 6,091,987 | A | 7/2000 | Thompson | 6,381,496 B1 | 4/2002 | Meadows et al. |
| 6,093,156 | A | 7/2000 | Cunningham et al. | 6,387,048 B1 | 5/2002 | Schulman et al. |
| 6,093,172 | A | 7/2000 | Funderburk et al. | 6,393,318 B1 | 5/2002 | Conn et al. |
| 6,103,033 | A | 8/2000 | Say et al. | 6,400,974 B1 | 6/2002 | Lesho |
| 6,120,676 | A | 9/2000 | Heller et al. | 6,403,944 B1 | 6/2002 | MacKenzie et al. |
| 6,121,009 | A | 9/2000 | Heller et al. | 6,405,066 B1 | 6/2002 | Essenpreis et al. |
| 6,129,823 | A | 10/2000 | Hughes et al. | 6,408,402 B1 | 6/2002 | Norman |
| 6,130,623 | A | 10/2000 | MacLellan et al. | 6,413,393 B1 | 7/2002 | Van Antwerp et al. |
| 6,132,371 | A | 10/2000 | Dempsey et al. | 6,416,471 B1 | 7/2002 | Kumar et al. |
| 6,134,461 | A | 10/2000 | Say et al. | 6,417,074 B2 | 7/2002 | Kopley et al. |
| 6,142,939 | A | 11/2000 | Eppstein et al. | 6,418,332 B1 | 7/2002 | Mastrototaro et al. |
| 6,143,164 | A | 11/2000 | Heller et al. | 6,418,346 B1 | 7/2002 | Nelson et al. |
| 6,144,303 | A | 11/2000 | Federman | 6,419,642 B1 | 7/2002 | Marchitto et al. |
| 6,144,869 | A | 11/2000 | Berner et al. | 6,425,829 B1 | 7/2002 | Julien |
| 6,144,871 | A | 11/2000 | Saito et al. | 6,427,088 B1 | 7/2002 | Bowman, IV et al. |
| 6,144,922 | A | 11/2000 | Douglas et al. | 6,432,585 B1 | 8/2002 | Kawakami et al. |
| 6,147,342 | A | 11/2000 | Kucher | 6,437,379 B2 | 8/2002 | Kopley et al. |
| 6,154,855 | A | 11/2000 | Norman | 6,438,385 B1 | 8/2002 | Heinonen et al. |
| 6,155,992 | A | 12/2000 | Henning et al. | 6,438,414 B1 | 8/2002 | Conn et al. |

| Patent | Type | Date | Inventor |
|---|---|---|---|
| 6,442,413 | B1 | 8/2002 | Silver |
| 6,445,374 | B2 | 9/2002 | Albert et al. |
| 6,461,329 | B1 | 10/2002 | Van Antwerp et al. |
| 6,462,162 | B2 | 10/2002 | Van Antwerp et al. |
| 6,464,848 | B1 | 10/2002 | Matsumoto |
| 6,466,807 | B1 | 10/2002 | Dobson et al. |
| 6,466,810 | B1 | 10/2002 | Ward et al. |
| 6,468,222 | B1 | 10/2002 | Mault et al. |
| 6,471,980 | B2 | 10/2002 | Sirhan et al. |
| 6,472,991 | B1 | 10/2002 | Schulman et al. |
| 6,475,196 | B1 | 11/2002 | Vachon |
| 6,478,736 | B1 | 11/2002 | Mault |
| 6,480,730 | B2 | 11/2002 | Darrow et al. |
| 6,482,158 | B2 | 11/2002 | Mault |
| 6,482,176 | B1 | 11/2002 | Wich |
| 6,484,045 | B1 | 11/2002 | Holker et al. |
| 6,484,046 | B1 | 11/2002 | Say et al. |
| 6,485,138 | B1 | 11/2002 | Kubota et al. |
| 6,485,461 | B1 | 11/2002 | Mason et al. |
| 6,485,465 | B2 | 11/2002 | Moberg et al. |
| 6,492,180 | B2 | 12/2002 | Brown et al. |
| 6,496,729 | B2 | 12/2002 | Thompson |
| 6,497,655 | B1 | 12/2002 | Linberg et al. |
| 6,498,043 | B1 | 12/2002 | Schulman et al. |
| 6,506,168 | B1 | 1/2003 | Fathallah et al. |
| 6,513,532 | B2 | 2/2003 | Mault et al. |
| 6,514,460 | B1 | 2/2003 | Fendrock |
| 6,514,689 | B2 | 2/2003 | Han et al. |
| 6,514,718 | B2 | 2/2003 | Heller et al. |
| 6,520,326 | B2 | 2/2003 | McIvor et al. |
| 6,522,530 | B2 | 2/2003 | Bang |
| 6,525,330 | B2 | 2/2003 | Paolini et al. |
| 6,526,298 | B1 | 2/2003 | Khalil et al. |
| 6,529,772 | B2 | 3/2003 | Carlson et al. |
| 6,530,915 | B1 | 3/2003 | Eppstein et al. |
| 6,535,753 | B1 | 3/2003 | Raskas |
| 6,537,243 | B1 | 3/2003 | Henning et al. |
| 6,540,675 | B2 | 4/2003 | Aceti et al. |
| 6,540,891 | B1 | 4/2003 | Stewart et al. |
| 6,543,224 | B1 | 4/2003 | Barooah |
| 6,544,212 | B2 | 4/2003 | Galley et al. |
| 6,546,269 | B1 | 4/2003 | Kurnik |
| 6,549,796 | B2 | 4/2003 | Sohrab |
| 6,551,276 | B1 | 4/2003 | Mann et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,975 | B1 | 5/2003 | Pool et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,564,807 | B1 | 5/2003 | Schulman et al. |
| 6,565,509 | B1 | 5/2003 | Say et al. |
| 6,565,738 | B1 | 5/2003 | Henning et al. |
| 6,569,157 | B1 | 5/2003 | Shain et al. |
| 6,571,128 | B2 | 5/2003 | Lebel et al. |
| 6,571,200 | B1 | 5/2003 | Mault |
| 6,574,510 | B2 | 6/2003 | Von Arx et al. |
| 6,576,117 | B1 | 6/2003 | Iketaki et al. |
| 6,577,899 | B2 | 6/2003 | Lebel et al. |
| 6,579,231 | B1 | 6/2003 | Phipps |
| 6,579,498 | B1 | 6/2003 | Eglise |
| 6,579,690 | B1 | 6/2003 | Bonnacaze et al. |
| 6,582,393 | B2 | 6/2003 | Sage, Jr. |
| 6,585,644 | B2 | 7/2003 | Lebel et al. |
| 6,586,971 | B1 | 7/2003 | Naffziger et al. |
| 6,587,705 | B1 | 7/2003 | Kim et al. |
| 6,589,229 | B1 | 7/2003 | Connelly et al. |
| 6,594,514 | B2 | 7/2003 | Berner et al. |
| 6,595,919 | B2 | 7/2003 | Berner et al. |
| 6,596,016 | B1 | 7/2003 | Vreman et al. |
| 6,600,997 | B2 | 7/2003 | Deweese et al. |
| 6,602,469 | B1 | 8/2003 | Maus et al. |
| 6,607,509 | B2 | 8/2003 | Bobroff et al. |
| 6,610,012 | B2 | 8/2003 | Mault |
| 6,612,306 | B1 | 9/2003 | Mault |
| 6,615,061 | B1 | 9/2003 | Khalil et al. |
| 6,615,074 | B2 | 9/2003 | Mickle et al. |
| 6,618,603 | B2 | 9/2003 | Varalli et al. |
| 6,620,106 | B2 | 9/2003 | Mault |
| 6,623,501 | B2 | 9/2003 | Heller et al. |
| 6,629,934 | B2 | 10/2003 | Mault et al. |
| 6,633,095 | B1 | 10/2003 | Swope et al. |
| 6,633,772 | B2 | 10/2003 | Ford et al. |
| 6,635,014 | B2 | 10/2003 | Starkweather et al. |
| 6,635,167 | B1 | 10/2003 | Richards et al. |
| 6,641,533 | B2 | 11/2003 | Causey, III et al. |
| 6,645,142 | B2 | 11/2003 | Braig et al. |
| 6,648,821 | B2 | 11/2003 | Lebel et al. |
| 6,650,064 | B2 | 11/2003 | Guthrie et al. |
| 6,653,091 | B1 | 11/2003 | Dunn et al. |
| 6,656,158 | B2 | 12/2003 | Mahoney et al. |
| 6,656,159 | B2 | 12/2003 | Flaherty |
| 6,659,948 | B2 | 12/2003 | Lebel et al. |
| 6,659,980 | B2 | 12/2003 | Moberg et al. |
| 6,668,196 | B1 | 12/2003 | Villegas et al. |
| 6,669,663 | B1 | 12/2003 | Thompson |
| 6,669,669 | B2 | 12/2003 | Flaherty et al. |
| 6,670,806 | B2 | 12/2003 | Wendt et al. |
| 6,679,841 | B2 | 1/2004 | Bojan et al. |
| 6,687,522 | B2 | 2/2004 | Tamada |
| 6,687,546 | B2 | 2/2004 | Lebel et al. |
| 6,692,457 | B2 | 2/2004 | Flaherty |
| 6,694,191 | B2 | 2/2004 | Starkweather et al. |
| 6,695,885 | B2 | 2/2004 | Schulman et al. |
| 6,699,218 | B2 | 3/2004 | Flaherty et al. |
| 6,702,857 | B2 | 3/2004 | Brauker et al. |
| 6,723,072 | B2 | 4/2004 | Flaherty et al. |
| 6,728,560 | B2 | 4/2004 | Kollias et al. |
| 6,730,200 | B1 | 5/2004 | Stewart et al. |
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,736,777 | B2 | 5/2004 | Kim et al. |
| 6,736,797 | B1 | 5/2004 | Larsen et al. |
| 6,738,654 | B2 | 5/2004 | Sohrab |
| 6,740,059 | B2 | 5/2004 | Flaherty |
| 6,740,075 | B2 | 5/2004 | Lebel et al. |
| 6,741,877 | B1 | 5/2004 | Shults et al. |
| 6,743,635 | B2 | 6/2004 | Neel et al. |
| 6,746,582 | B2 | 6/2004 | Heller et al. |
| 6,749,587 | B2 | 6/2004 | Flaherty |
| 6,752,785 | B2 | 6/2004 | Van Antwerp et al. |
| 6,752,787 | B1 | 6/2004 | Causey, III et al. |
| 6,758,810 | B2 | 7/2004 | Lebel et al. |
| 6,764,581 | B1 | 7/2004 | Forrow et al. |
| 6,768,425 | B2 | 7/2004 | Flaherty et al. |
| 6,770,030 | B1 | 8/2004 | Schaupp et al. |
| 6,770,729 | B2 | 8/2004 | Van Antwerp |
| 6,773,563 | B2 | 8/2004 | Matsumoto |
| 6,779,984 | B2 | 8/2004 | Lilie et al. |
| 6,789,195 | B1 | 9/2004 | Prihoda et al. |
| 6,790,178 | B1 | 9/2004 | Mault et al. |
| 6,794,195 | B2 | 9/2004 | Colvin, Jr. |
| 6,799,861 | B2 | 10/2004 | Naghi et al. |
| 6,804,558 | B2 | 10/2004 | Haller et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,816,742 | B2 | 11/2004 | Kim et al. |
| 6,818,348 | B1 | 11/2004 | Venkatesan et al. |
| 6,830,558 | B2 | 12/2004 | Flaherty et al. |
| 6,832,114 | B1 | 12/2004 | Whitehurst et al. |
| 6,833,540 | B2 | 12/2004 | MacKenzie et al. |
| 6,835,553 | B2 | 12/2004 | Han et al. |
| 6,837,858 | B2 | 1/2005 | Cunningham et al. |
| 6,839,596 | B2 | 1/2005 | Nelson et al. |
| 6,840,912 | B2 | 1/2005 | Kloepfer et al. |
| 6,849,237 | B2 | 2/2005 | Housefield et al. |
| 6,850,790 | B2 | 2/2005 | Berner et al. |
| 6,859,831 | B1 | 2/2005 | Gelvin et al. |
| 6,862,465 | B2 | 3/2005 | Shults et al. |
| 6,872,200 | B2 | 3/2005 | Mann et al. |
| 6,873,268 | B2 * | 3/2005 | Lebel et al. ............ 340/870.16 |

| Patent No. | Date | Inventor |
|---|---|---|
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,927,749 B1 | 8/2005 | Klemm |
| 6,931,327 B2 | 8/2005 | Goode, Jr. et al. |
| 6,936,029 B2 | 8/2005 | Mann et al. |
| 6,940,403 B2 | 9/2005 | Kail, IV |
| 6,941,163 B2 | 9/2005 | Ford et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,961,448 B2 | 11/2005 | Nichols et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,009,511 B2 | 3/2006 | Mazar et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stivoric et al. |
| 7,024,236 B2 | 4/2006 | Ford et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,251 B2 | 5/2006 | Nason et al. |
| 7,058,437 B2 | 6/2006 | Buse et al. |
| 7,058,453 B2 | 6/2006 | Nelson et al. |
| 7,060,031 B2 | 6/2006 | Webb et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,082,334 B2 | 7/2006 | Boute et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,125,382 B2 | 10/2006 | Zhou et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,167,818 B2 | 1/2007 | Brown |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,193,521 B2 | 3/2007 | Moberg et al. |
| 7,198,603 B2 | 4/2007 | Penner et al. |
| 7,202,734 B1 | 4/2007 | Raab |
| 7,203,549 B2 | 4/2007 | Schommer et al. |
| 7,205,409 B2 | 4/2007 | Pei et al. |
| 7,207,974 B2 | 4/2007 | Safabash et al. |
| 7,208,119 B1 | 4/2007 | Kurtock et al. |
| 7,211,048 B1 | 5/2007 | Najafi et |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,666 B2 | 8/2007 | Brown |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,283,867 B2 | 10/2007 | Strother et al. |
| 7,291,497 B2 | 11/2007 | Holmes et al. |
| 7,295,867 B2 | 11/2007 | Berner et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,323,091 B1 | 1/2008 | Gillette et al. |
| 7,324,850 B2 | 1/2008 | Persen et al. |
| 7,324,949 B2 | 1/2008 | Bristol |
| 7,343,188 B2 | 3/2008 | Sohrab |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,371,247 B2 | 5/2008 | Boecker et al. |
| 7,379,765 B2 | 5/2008 | Petisce et al. |
| 7,384,397 B2 | 6/2008 | Zhang et al. |
| 7,387,010 B2 | 6/2008 | Sunshine |
| 7,399,277 B2 | 7/2008 | Saidara et al. |
| 7,419,573 B2 | 9/2008 | Gundel |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,565,197 B2 | 7/2009 | Haubrich et al. |
| 7,574,266 B2 | 8/2009 | Dudding et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |

| | | |
|---|---|---|
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,741,734 B2 | 6/2010 | Joannopoulos et al. |
| 7,768,408 B2 | 8/2010 | Reggiardo et al. |
| 7,771,352 B2 | 8/2010 | Shults et al. |
| 7,774,145 B2 | 8/2010 | Brauker et al. |
| 7,778,795 B2 | 8/2010 | Fukushima et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode, Jr. et al. |
| 7,831,310 B2 | 11/2010 | Lebel et al. |
| 7,850,621 B2 | 12/2010 | Briggs et al. |
| 7,860,574 B2 | 12/2010 | Von Arx et al. |
| 7,882,611 B2 | 2/2011 | Shah et al. |
| 7,884,729 B2 | 2/2011 | Reggiardo et al. |
| 7,899,511 B2 | 3/2011 | Shults et al. |
| 7,905,833 B2 | 3/2011 | Brister et al. |
| 7,911,010 B2 | 3/2011 | Stetter |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,922,458 B2 | 4/2011 | Rush et al. |
| 7,954,385 B2 | 6/2011 | Raisanen |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,047,811 B2 | 11/2011 | Rush et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0034617 A1 | 10/2001 | Kimata |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0019612 A1 | 2/2002 | Watanabe et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0065682 A1 | 5/2002 | Goldenberg |
| 2002/0068858 A1 | 6/2002 | Braig et al. |
| 2002/0072784 A1 | 6/2002 | Sheppard et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | VanAntwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0169439 A1 | 11/2002 | Flaherty et al. |
| 2002/0177764 A1 | 11/2002 | Sohrab |
| 2002/0193679 A1 | 12/2002 | Malave et al. |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0055380 A1 | 3/2003 | Flaherty et al. |
| 2003/0060692 A1 | 3/2003 | Ruchti et al. |
| 2003/0060765 A1 | 3/2003 | Campbell et al. |
| 2003/0065254 A1 | 4/2003 | Schulman et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnecaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0118460 A1 | 6/2003 | Lilie et al. |
| 2003/0130616 A1 | 7/2003 | Steil et al. |
| 2003/0134347 A1 | 7/2003 | Heller et al. |
| 2003/0135100 A1 | 7/2003 | Kim et al. |

| | | |
|---|---|---|
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0154405 A1 | 8/2003 | Harrison |
| 2003/0158472 A1 | 8/2003 | Sohrab |
| 2003/0158707 A1 | 8/2003 | Doi |
| 2003/0167035 A1 | 9/2003 | Flaherty et al. |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0214304 A1 | 11/2003 | Karinka et al. |
| 2003/0217966 A1 | 11/2003 | Tapsak et al. |
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0030226 A1 | 2/2004 | Quy |
| 2004/0039256 A1 | 2/2004 | Kawatahara et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0059284 A1 | 3/2004 | Nash et al. |
| 2004/0064088 A1 | 4/2004 | Gorman et al. |
| 2004/0064096 A1 | 4/2004 | Flaherty et al. |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0153032 A1 | 8/2004 | Garribotto et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0254884 A1 | 12/2004 | Haber et al. |
| 2004/0263354 A1 | 12/2004 | Mann et al. |
| 2004/0264396 A1 | 12/2004 | Ginzburg et al. |
| 2005/0003470 A1 * | 1/2005 | Nelson et al. .................... 435/14 |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1 | 4/2005 | Malave et al. |
| 2005/0112169 A1 | 5/2005 | Brauker et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0218880 A1 | 10/2005 | Ioffe |
| 2005/0235732 A1 | 10/2005 | Rush |
| 2005/0238503 A1 | 10/2005 | Rush et al. |

| | | |
|---|---|---|
| 2005/0238507 A1 | 10/2005 | DiIanni et al. |
| 2005/0239154 A1 | 10/2005 | Feldman et al. |
| 2005/0239518 A1 | 10/2005 | D'Agostino et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0249506 A1 | 11/2005 | Fuse |
| 2005/0249606 A1 | 11/2005 | Rush |
| 2005/0251083 A1 | 11/2005 | Carr-Brendel et al. |
| 2005/0261660 A1 | 11/2005 | Choi |
| 2005/0267550 A1 | 12/2005 | Hess et al. |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 * | 1/2006 | Kraft et al. ............... 340/539.12 |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0004603 A1 | 1/2006 | Peterka et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartkowiak et al. |
| 2006/0074564 A1 | 4/2006 | Bartkowiak et al. |
| 2006/0094986 A1 | 5/2006 | Neel et al. |
| 2006/0154642 A1 | 7/2006 | Scannell |
| 2006/0161078 A1 | 7/2006 | Schraga |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0202805 A1 | 9/2006 | Schulman et al. |
| 2006/0222566 A1 | 10/2006 | Brauker et al. |
| 2006/0224141 A1 | 10/2006 | Rush et al. |
| 2006/0240403 A1 | 10/2006 | List et al. |
| 2006/0247508 A1 | 11/2006 | Fennell |
| 2006/0247710 A1 | 11/2006 | Goetz et al. |
| 2006/0253085 A1 | 11/2006 | Geismar et al. |
| 2006/0253086 A1 | 11/2006 | Moberg et al. |
| 2006/0273759 A1 | 12/2006 | Reggiardo |
| 2006/0282290 A1 | 12/2006 | Flaherty et al. |
| 2006/0287691 A1 | 12/2006 | Drew |
| 2006/0293577 A1 | 12/2006 | Morrison et al. |
| 2007/0016381 A1 | 1/2007 | Kamath et al. |
| 2007/0032717 A1 | 2/2007 | Brister et al. |
| 2007/0055799 A1 | 3/2007 | Koehler et al. |
| 2007/0078323 A1 | 4/2007 | Reggiardo et al. |
| 2007/0078818 A1 | 4/2007 | Zivitz et al. |
| 2007/0100222 A1 | 5/2007 | Mastrototaro et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0156033 A1 | 7/2007 | Causey, III et al. |
| 2007/0163880 A1 | 7/2007 | Woo et al. |
| 2007/0173711 A1 | 7/2007 | Shah et al. |
| 2007/0176867 A1 | 8/2007 | Reggiardo et al. |
| 2007/0203966 A1 | 8/2007 | Brauker et al. |
| 2007/0219480 A1 | 9/2007 | Kamen et al. |
| 2007/0219597 A1 | 9/2007 | Kamen et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0253021 A1 | 11/2007 | Mehta et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0285238 A1 | 12/2007 | Batra |
| 2008/0018433 A1 | 1/2008 | Pitt-Pladdy |
| 2008/0021666 A1 | 1/2008 | Goode, Jr. et al. |
| 2008/0030369 A1 | 2/2008 | Mann et al. |
| 2008/0033254 A1 | 2/2008 | Kamath et al. |
| 2008/0045824 A1 | 2/2008 | Tapsak et al. |
| 2008/0064941 A1 | 3/2008 | Funderburk et al. |
| 2008/0064943 A1 | 3/2008 | Talbot et al. |
| 2008/0071156 A1 | 3/2008 | Brister et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097918 A1 | 4/2008 | Spector et al. |
| 2008/0103447 A1 | 5/2008 | Reggiardo et al. |
| 2008/0108942 A1 | 5/2008 | Brister et al. |
| 2008/0119703 A1 | 5/2008 | Brister et al. |
| 2008/0119705 A1 | 5/2008 | Patel et al. |
| 2008/0139910 A1 | 6/2008 | Mastrototaro et al. |
| 2008/0167572 A1 | 7/2008 | Stivoric et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200838 A1 | 8/2008 | Goldberger et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0235469 A1 | 9/2008 | Drew |
| 2008/0242961 A1 | 10/2008 | Brister et al. |
| 2008/0255438 A1 | 10/2008 | Saidara et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312844 A1 | 12/2008 | Hayter et al. |
| 2009/0005666 A1 | 1/2009 | Shin et al. |

| | | |
|---|---|---|
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063196 A1 | 3/2009 | Frederickson |
| 2009/0063402 A1 | 3/2009 | Hayter |
| 2009/0068954 A1 | 3/2009 | Reggiardo et al. |
| 2009/0069750 A1 | 3/2009 | Schraga |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0216553 A1 | 8/2009 | Cellura |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0259118 A1 | 10/2009 | Feldman et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0190435 A1 | 7/2010 | Cook et al. |
| 2010/0241447 A1 | 9/2010 | Siniaguine et al. |
| 2011/0004276 A1 | 1/2011 | Blair et al. |
| 2011/0152637 A1 | 6/2011 | Kateraas et al. |

FOREIGN PATENT DOCUMENTS

| | | |
|---|---|---|
| EP | 0455455 | 11/1991 |
| EP | 0465708 | 1/1992 |
| EP | 0724859 | 8/1996 |
| EP | 0878707 | 11/1998 |
| EP | 0678308 | 5/2000 |
| EP | 0543916 | 7/2001 |
| EP | 1130638 | 9/2001 |
| EP | 0980688 | 12/2002 |
| EP | 1292218 | 3/2003 |
| EP | 1077634 | 7/2003 |
| EP | 1755443 | 11/2005 |
| EP | 1666091 | 6/2006 |
| EP | 1703697 | 9/2006 |
| EP | 1704893 | 9/2006 |
| EP | 1783536 | 5/2007 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 1448489 | 8/2010 |
| EP | 1971396 | 8/2010 |
| JP | 2001-177423 | 6/2001 |
| JP | 2001-056673 | 11/2001 |
| WO | WO-97/33513 | 9/1997 |
| WO | WO-99/22236 | 5/1999 |
| WO | WO-99/56613 | 11/1999 |
| WO | WO-00/74753 | 12/2000 |
| WO | WO-01/41849 | 6/2001 |
| WO | WO-01/52727 | 7/2001 |
| WO | WO-01/54753 | 8/2001 |
| WO | WO-02/058537 | 8/2002 |
| WO | WO-02/084860 | 10/2002 |
| WO | WO-03/053503 | 7/2003 |
| WO | WO-2004/028337 | 4/2004 |
| WO | WO-2004/032994 | 4/2004 |
| WO | WO-2004/061420 | 7/2004 |
| WO | WO-2005/045744 | 5/2005 |
| WO | WO-2005/089103 | 9/2005 |
| WO | WO-2005/101994 | 11/2005 |
| WO | WO-2006/003919 | 1/2006 |
| WO | WO-2006/032653 | 3/2006 |
| WO | WO-2006/079114 | 7/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/124099 | 11/2006 |
| WO | WO-2006/132884 | 12/2006 |
| WO | WO-2007/041072 | 4/2007 |
| WO | WO-2007/090037 | 8/2007 |
| WO | WO-2008/055037 | 5/2008 |
| WO | WO-2008/086541 | 7/2008 |
| WO | WO-2008/110267 | 9/2008 |
| WO | WO-2011/022418 | 2/2011 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

U.S. Appl. No. 11/383,945, Notice of Allowance mailed Jun. 18, 2010.

U.S. Appl. No. 11/383,945, Office Action mailed Dec. 16, 2009.

U.S. Appl. No. 11/383,945, Office Action mailed Jun. 8, 2009.
U.S. Appl. No. 11/383,945, Office Action mailed Oct. 31, 2008.
U.S. Appl. No. 12/849,007, Notice of Allowance mailed Nov. 16, 2010.
U.S. Appl. No. 12/849,007, Office Action mailed Oct. 18, 2010.
U.S. Appl. No. 13/022,610, Notice of Allowance mailed Nov. 15, 2011.
U.S. Appl. No. 13/022,610, Office Action mailed Oct. 20, 2011.

* cited by examiner

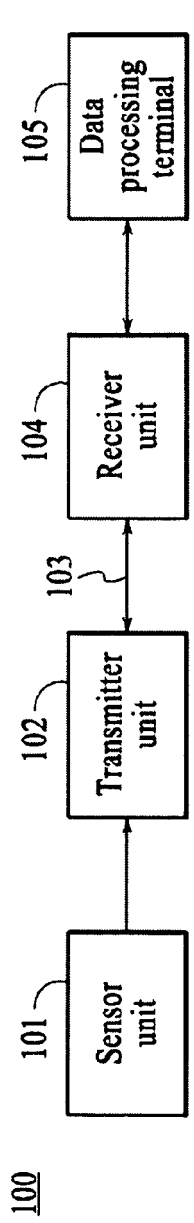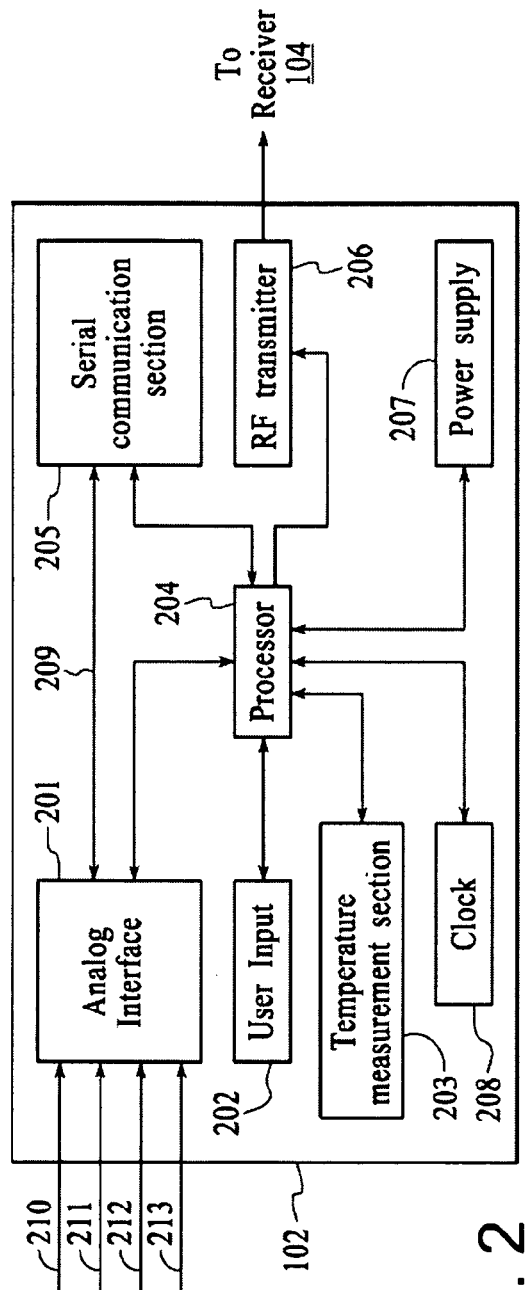

METHOD AND SYSTEM FOR PROVIDING DATA MANAGEMENT IN DATA MONITORING SYSTEM

RELATED APPLICATIONS

This application is a continuation of U.S. application Ser. No. 13/022,610 filed Feb. 7, 2011, which is a continuation of U.S. application Ser. No. 12/849,007 filed Aug. 2, 2010, now U.S. Pat. No. 7,884,729, which is a continuation of U.S. application Ser. No. 11/383,945 filed May 17, 2006, now U.S. Pat. No. 7,768,408, which claims the benefit of U.S. Provisional Application No. 60/681,942 filed on May 17, 2005, entitled "Method and System for Providing Data Management in Data Monitoring System", the disclosures of each of which are incorporated herein by reference for all purposes.

BACKGROUND

Data monitoring and management systems such as continuous or semi-continuous analyte monitoring systems are typically configured to process a large amount of data and/or transmit the data over a network via a cabled or wireless connection. Such systems typically include devices such as data transmission devices and data reception devices which are configured to communicate with each other in a time sensitive fashion (e.g. to provide substantially real-time data). For the data monitoring and management system to properly function, each device or unit in the system needs to be in operational mode. That is, when one component or device is not properly functioning, or is not optimized for performance in the system, the entire system may be adversely impacted.

Typical devices or components in such systems generally are under the control of a microprocessor or an equivalent device which controls the functionality and maintenance of the device. As more features and functions are added and incorporated into the device or component in the data monitoring and management system, the microprocessor is required to handle the additional processing which imposes a heavy load upon the microprocessor, and in addition, increases the potential for failure modes, effectively disabling the device or component in the system.

In view of the foregoing, it would be desirable to have a fault tolerant data monitoring and management system such as in continuous analyte monitoring systems for efficient data monitoring and management.

SUMMARY OF THE INVENTION

In view of the foregoing, in accordance with the various embodiments of the present invention, there is provided a fault tolerant data receiver unit configured with partitioned or separate processing units, each configured to perform a predetermined and/or specific processing associated with the one or more substantially non-overlapping functions of the data monitoring and management system. In one embodiment, the data receiver unit includes a communication module, a user interface module and a sample analysis module, and each module is provided with a separate processing unit. In this manner, in one embodiment, each module is configured to perform predetermined functions associated with the data monitoring and management system to provide a modular, objected oriented processing architecture.

These and other objects, features and advantages of the present invention will become more fully apparent from the following detailed description of the embodiments, the appended claims and the accompanying drawings.

BRIEF DESCRIPTION OF THE DRAWINGS

FIG. 1 illustrates a data monitoring and management system such as, for example, an analyte monitoring system 100 for practicing one embodiment of the present invention;

FIG. 2 is a block diagram of the transmitter unit of the data monitoring and management system shown in FIG. 1 in accordance with one embodiment of the present invention;

DETAILED DESCRIPTION

Figure 3:
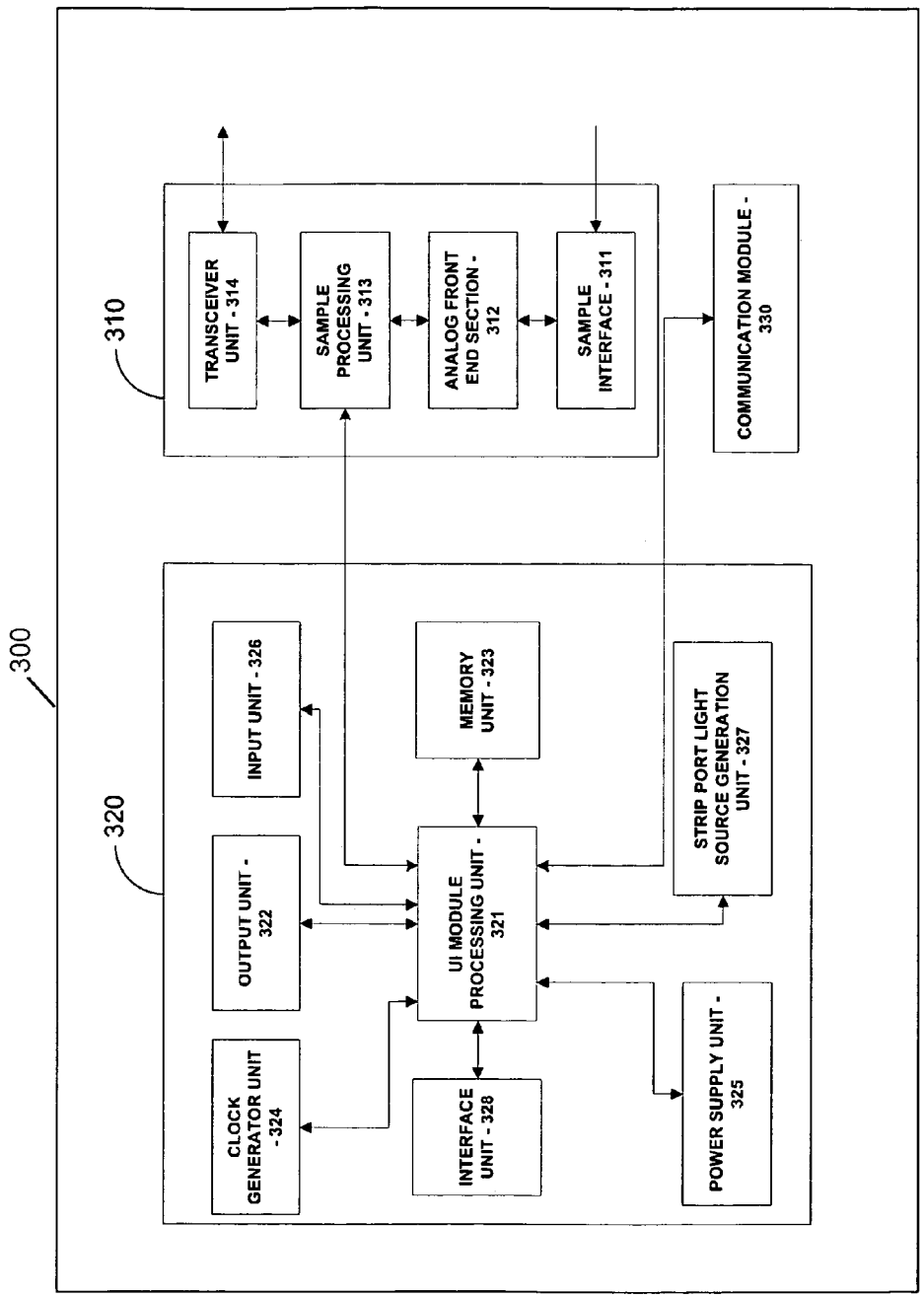
FIG. 3 illustrates the receiver unit of the data monitoring and management system shown in FIG. 1 in accordance with one embodiment of the present invention.

As described in detail below, in accordance with the various embodiments of the present invention, there is provided a fault tolerant data receiver unit configured with a partitioned or separate processing units, each configured to perform a predetermined and/or specific processing associated with the one or more substantially non-overlapping functions of the data monitoring and management system. In one embodiment, the data receiver unit includes a communication module, a user interface module and a sample analysis module, and each module provided with a separate processing unit. In this manner, in one embodiment, each module is configured to perform predetermined functions associated with the data monitoring and management system to provide a modular, object oriented processing architecture.

FIG. 1 illustrates a data monitoring and management system such as, for example, an analyte monitoring system 100 for practicing one embodiment of the present invention. In such embodiment, the analyte monitoring system 100 includes an analyte sensor 101, a transmitter unit 102 coupled to the sensor 101, and a receiver unit 104 which is configured to communicate with the transmitter unit 102 via a communication link 103. The receiver unit 104 may be further configured to transmit data to a data processing terminal 105 for evaluating the data received by the receiver unit 104.

Only one sensor 101, transmitter unit 102, communication link 103, receiver unit 104, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, receiver unit 104, and data processing terminal 105, where each receiver unit 104 is uniquely synchronized with a respective transmitter unit 102. Moreover, within the scope of the present invention, the analyte monitoring system 100 may be a continuous monitoring system, or a semi-continuous or discrete monitoring system.

In one embodiment of the present invention, the sensor 101 is physically positioned on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a sampled glucose level of the user, for transmission to the receiver unit 104 via the communication link 103.

Additional analytes that may be monitored or determined by sensor 101 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

In one embodiment, the analyte monitoring system 100 is configured as a one-way RF communication path from the transmitter unit 102 to the receiver unit 104. In such embodiment, the transmitter unit 102 transmits the sampled data signals received from the sensor 101 without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals. Alternatively, the analyte monitoring system 100 may be configured with a bi-directional RF communication between the transmitter unit 102 and the receiver unit 104.

Additionally, in one aspect, the receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the receiver unit 104 is a data processing section which is configured to process the data signals received from the transmitter unit 102 such as by performing data decoding, error detection and correction, data clock generation, and data bit recovery.

In operation, upon completing the power-on procedure, the receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the receiver unit 104 is configured to begin receiving from the transmitter unit 102 data signals corresponding to the user's detected analyte level. More specifically, the receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump (external or implantable), which may be configured to administer insulin to patients, and which is configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses (e.g., correction bolus, carbohydrate bolus, dual wave bolus including normal and extended bolus such as square wave bolus, and so on) for administration based on, among others, the detected analyte levels received from the transmitter unit 102.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts comprised of the working electrode (W) 210, the guard contact (G) 211, the reference electrode (R) 212, and the counter electrode (C) 213, each operatively coupled to the analog interface 201 of the transmitter unit 102 for connection to the sensor unit 101 (FIG. 1). In one embodiment, the working electrode (W) 210 and reference electrode (R) 212 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the receiver 104 under the control of the transmitter processor 204. Furthermore, the power supply 207 may include a commercially available battery.

The transmitter unit 102 is also configured such that the power supply section 207 is capable of providing power to the transmitter for a minimum of three months of continuous operation after having been stored for 18 months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Additional detailed description of the analyte monitoring system, its various components including the functional descriptions of the transmitter unit are provided in U.S. Pat. Nos. 6,175,752 and 7,811,231, the disclosures of each of which are incorporated herein by reference for all purposes.

FIG. 3 illustrates the receiver unit of the data monitoring and management system shown in FIG. 1 in accordance with one embodiment of the present invention. Referring to FIG. 3, the receiver unit 300 in one embodiment of the present invention includes a sample analysis module 310, a user interface (UI) module 320, and a communication module 330. In one embodiment, the sample analysis module 310 includes a sample interface 311 which is configured to receive a discrete sample for processing. For example, the sample interface 311 may in one embodiment include a strip port configured to receive a blood glucose strip with a blood sample provided thereon for processing.

Referring back to FIG. 3, the sample analysis module 310 is also provided with an analog front end section 312 which is configured to, among others, process the sample received from the sample interface 311 to convert one or more analog signals associated with the acquired sample characteristics (such as blood glucose level determined from the blood sample received by the sample interface 311) into a corresponding one or more digital signals for further processing.

The analog front end section 312 in one embodiment is further operatively coupled to a sample analysis processing unit 313 which is configured, in one embodiment, to process the data received from the analog front end section 312. Within the scope of the present invention, the sample analysis processing unit 313 is configured to perform data processing associated with sample related data. For example, in one embodiment of the present invention, the sample analysis processing unit 313 may be configured to perform substantially all of the data processing associated with the discretely measured blood glucose data in addition to the continuous glucose data received from the transmitter unit 102 (FIG. 1).

In one embodiment of the present invention, the transceiver unit 314 of the sample analysis module 310 is configured to receive analyte related data from the transmitter unit 102 (FIG. 1) which is coupled to the sensor 101 that is positioned in fluid contact with the patient's analytes. The transceiver unit 314 may be configured for unidirectional or bidirectional communication.

Referring still to FIG. 3, the sample analysis processing unit 313 in one embodiment is operatively coupled to a transceiver unit 314 to transmit data to a remote device, for example, to the data processing terminal 105 (or an infusion device, or a supplemental receiver/monitor) over a data connection including, for example, a wireless RF communication link, or a cabled connection such as a USB connection.

As discussed in further detail below, in one embodiment of the present invention, the sample analysis processing unit 313 of the sample analysis module 310 may include an MSP430 microprocessor (or any other functionally equivalent processing unit) to handle data processing associated with glucose data, in addition to RF data reception including performing data decoding on data received from the transmitter unit 102 (FIG. 1). In one aspect of the present invention, communication with the sample analysis module 310 is achieved with an asynchronous serial interface, and where the sample analysis module 310 may be configured to handle real time clock, power management, processing of continuous and discrete glucose data, monitoring and/or performing processing associated with the internal temperature, or as the UI watchdog.

Referring back to FIG. 3, the sample analysis processing unit 313 is operatively coupled to a UI module processing unit 321 of the UI module 320. In addition, the UI module processing unit 321 of the UI module 320 is also operatively coupled to the communication module 330. In one embodiment of the present invention, the communication module 330 includes a Bluetooth® module configured to communicate under the Bluetooth® transmission protocol and otherwise configured to meet the Bluetooth® communication protocol standard. Such Bluetooth® module has, for example, a built-in ARM processor to handle all aspects of the Bluetooth® protocol in an independent fashion from the sample analysis module 310, and the user interface (UI) module 320. In one embodiment, the UI module processing unit 321 is configured to communicate with the communication module 330 over an asynchronous serial interface.

Referring again to FIG. 3, the communication module 330 in another embodiment of the present invention include other types of communication devices that may be configured to provide communication functions compatible to the Bluetooth® module as described above. For example, a USB interface may be implemented with a TIUSB3410 chip available from Texas Instruments. The TIUSB3410 has a built-in R8051 processor to handle all aspects of the USB protocol in an independent fashion from the sample analysis module 310, and the user interface (UI) module 320. Other interface methods are available in modular form (i.e. with built-in processors that handle all aspects of the given protocol) such as, but not limited to WiFi, Home RF, various infrared such as IrDA, and various networking such as Ethernet Referring back again to FIG. 3, the UI module 320 in one embodiment of the present invention includes a UI module processing unit 321 which is configured to control the functionalities of the components of the UI module 320, as well as to communicate with the sample analysis module 310 and the communication module 330. The UI module 320 also includes an input unit 326, and output unit 322, a memory unit 323 (including, for example, both volatile and non-volatile memories), a strip port light source generation unit 327, a power supply unit 325, an interface unit 328, and a clock generator unit 324. As shown in FIG. 3, in one embodiment, each of these components of the UI module 320 are configured to perform the predetermined routines and/or processes under the control of the UI module processing unit 321.

For example, in one embodiment, the UI module processing unit 321 is configured to communicate with the sample analysis module 310 when a strip is inserted into the sample interface 311, and also with the communication module 330 for data communication. In addition, within the scope of the present invention, the UI module processing unit 321 in one embodiment is configured to update the output display on the output unit 322, process the received glucose data, maintain a data log (or device operational status log including error or failure mode logs), and perform power management in conjunction with the power supply unit 325.

More specifically, in one embodiment of the present invention, the UI module 320 is configured to operate as a peripheral device of the sample analysis module 310 with respect to power management. That is, the sample analysis module 310 power is not switched and remains valid as long as a power supply such as a battery with a predetermined signal level (for example, 1.8V) is installed, or alternatively, a supercapacitor is provided and configured to maintain the predetermined signal level. Further, the UI module 320 power is switched off when the power is low (for example, when the power signal level falls below a predetermined threshold level (such as 2.1 volts, for example)).

Additionally, in one embodiment, the sample analysis module 310 is configured to maintain the UI module 320 in a reset status until the operating state of all UI signals has been established. As such, the sample analysis module 310 may be configured to reset the UI module 320 each time it boots so that the sample analysis module 310 and the UI module 320 remain synchronized. In other words, in one embodiment of the present invention, the sample analysis module 310 may be configured as a microprocessor supervisor circuit with respect to the UI module 320.

In this manner, in one embodiment of the present invention, the data monitoring and management system 100 (FIG. 1) may include a modular configuration where data processing functions such as analyte related data processing and management of blood glucose data from a discrete sample acquisition device (such as a blood glucose meter) and continuous data stream received from the transmitter unit 102 coupled to the analyte sensor 101 (FIG. 1) are processed and analyzed by the sample analysis processing unit 313, while communication functions are handled by a separate communication module 330. Moreover, in one embodiment, other functionalities of the data monitoring and management system 100 (FIG. 1) such as user interface, clock signal generation and the like are handled by the UI module processing unit 321.

Referring yet again to FIG. 3, in one embodiment, the UI module processing unit 321 may be configured to run between approximately 5 MHz and 33.3 MHz. The output unit 322 may include a display unit which in one embodiment is a liquid crystal display (LCD). In one embodiment, the LCD display unit may be coupled to the bus on the UI module processing unit 321 as a memory mapped peripheral device. Likewise, in one aspect, the memory unit 323 may include an SRAM which is connected to the bus on the UI module processing unit 321 as a memory mapped peripheral device. In addition, the memory unit 323 may also include a non-volatile memory which may be configured to store the log information associated with the receiver unit 300. In one embodiment, the non-volatile memory may include an EEPROM with a serial peripheral interface to connect to the serial communication interface of the UI module processing unit 321.

Referring still to FIG. 3, the clock generator unit 324 of the receiver unit 300 may be configured to act as a supervisor and a clock generator to provide spread spectrum processor clock frequency dithering to lower the radiated emissions (EMC) of the user interface (UI) module 320. While the real time clock signals may be received from the sample analysis module 310, in one aspect, in the absence of the sample analysis module 310, the clock generator unit 324 may be configured to provide the real time clock signal in conjunction with, for example, a crystal oscillator.

Referring still to FIG. 3, the power supply unit 325 in one embodiment may include a disposable battery with fusing and ESD protection. When the disposable power supply reaches a near end of life status, a predefined signal may be generated which will trigger when the battery voltage signal falls below a predetermined level, for example, 2.1 Volts. Moreover, to recover from a severe processing load such as for example, when the communication module 330 (e.g., Bluetooth® module) triggers such signal for communication, a predetermined trigger level may be lowered so as to allow the UI module processing unit 321 to recover and maintain its functionality.

In addition, since the signals from the power supply unit 325 is used primarily for the UI module 320, the receiver unit 300 power consumption may be lowered significantly when the predefined signal associated with the power supply nearing end of life status is active, so that the sample analysis module 310 may be provided with substantially the maximum amount of power to maintain the real time clock and for failure mitigation. Moreover, the output signal from the power supply unit 325 in one embodiment is used by the communication module 330 and may be turned off when the communication module 330 is not in active communication mode to reduce quiescent current and to potentially increase the battery life.

Referring yet again to FIG. 3, the power supply unit 325 may be configured in one embodiment to supply power to the components of the receiver unit 300 as shown in the Figure. Referring yet again to FIG. 3, the input unit 326 may include buttons, touch sensitive screen, a jog wheel or any type of input device or mechanism to allow a user to input information or data into the receiver unit 300. In one embodiment, the input unit 326 may include a plurality of buttons, each of which are operatively coupled to the UI module processing unit 321. In one embodiment, the patient or the user may manipulate the input unit 326 to enter data or otherwise provide information so as to be responsive to any commands or signals generated by the receiver unit 300 that prompts for a user input.

In addition, the output unit 322 may include a backlight component which is configured to illuminate at least a portion of the output unit 322 in the case where the receiver unit 300 is used in a substantially dark environment. As shown, the output unit 322 is operatively coupled to the UI module processing unit 321, and accordingly, the output unit 322 may be configured to output display generated or analyzed data under the control of the UI module processing unit 321. Moreover, upon user activation or by automatic sensing mechanism, the output display 322 such as an LCD display unit may turn on the backlight feature so as to illuminate at least a portion of the output unit 322 to enable the patient to view the output unit 322 in substantially dark environment.

Furthermore, the output unit 322 may also include an audible output section such as speakers, and/or a physical output section, such as a vibratory alert mechanism. In one embodiment, the audio and vibratory alert mechanisms may be configured to operate under the control of the UI module processing unit 321, and also, under backup control by the sample analysis processing unit 313 of the sample analysis module 310. In this manner, even if the UI module processing unit fails, the sample analysis module 310 may be configured as a backup unit to control the output unit 322 for certain predetermined types of alarms and/or alerts thus providing a measure of fault tolerance for the system.

Referring yet still again to FIG. 3, the receiver unit 300 includes the strip port light source generation unit 327 which is operatively coupled to the UI module processing unit 321, and is configured in one embodiment to illuminate the sample interface 311 of the sample analysis module 310 such that, in substantially dark settings, the patient may still be able to check for blood glucose level easily by inserting the test strip with the blood sample thereon, into the sample interface 311 which may be illuminated by the strip port light source generation unit 327. The strip port light source generation unit 327 may also be used as a visual alert mechanism and may be configured to operate under the control of the UI module processing unit 321, and also, under backup control by the sample analysis processing unit 313 of the sample analysis module 310.

In addition, the interface unit 328 of the receiver unit 300 in one embodiment of the present invention may be configured as a cradle unit and/or a docking station. In addition, the interface unit 328 of the receiver unit 300 may be configured for test and/or diagnostic procedure interface to test or otherwise configure the receiver unit 300 via the interface unit 328 during or post manufacturing to ensure that the receiver unit 300 is properly configured.

Figure 4:
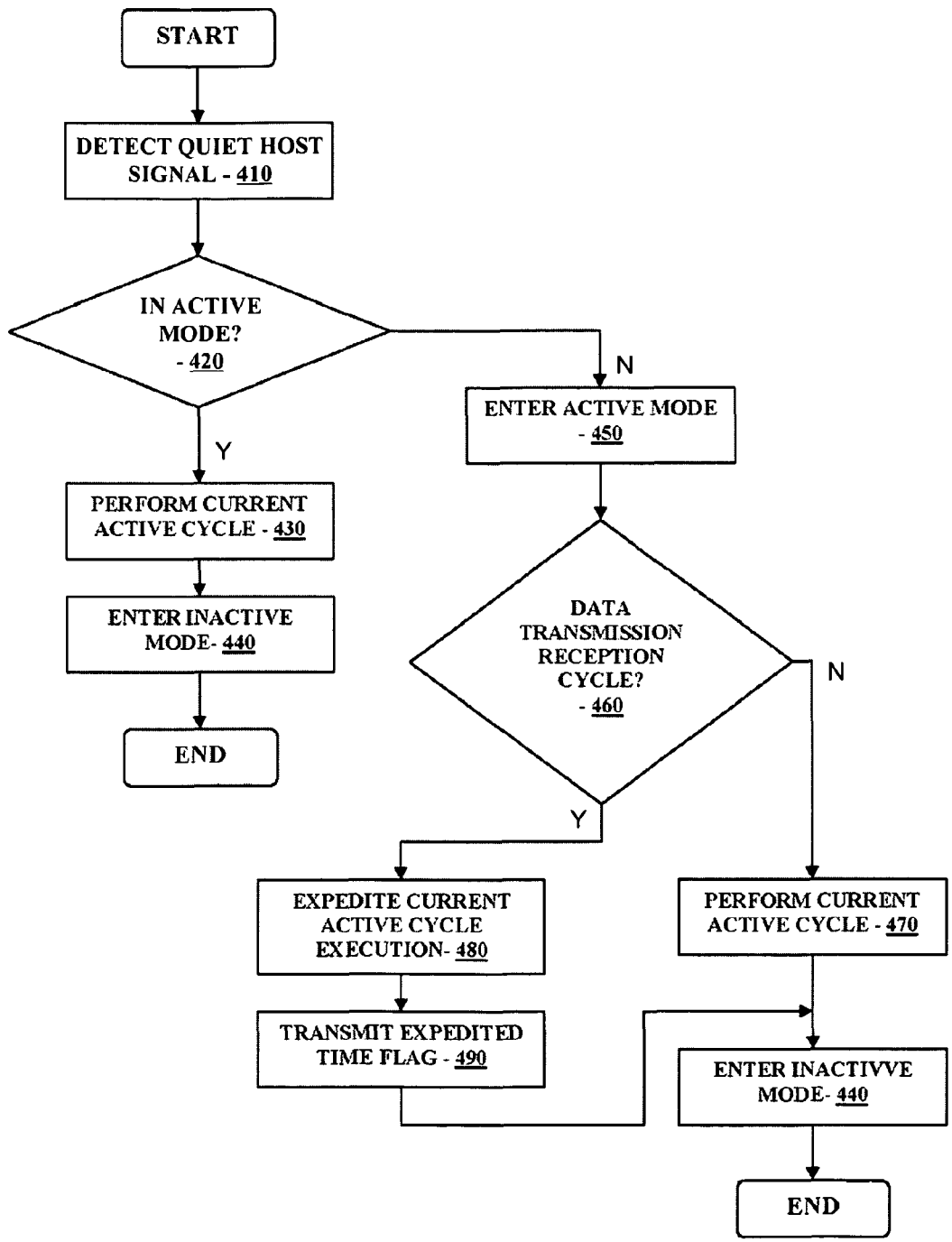
FIG. 4 is a flowchart illustrating the quiet host procedure in the receiver unit of the data monitoring and management system of FIG. 3 in accordance with one embodiment of the present invention.

FIG. 4 is a flowchart illustrating the quiet host procedure in the receiver unit of the data monitoring and management system of FIG. 3 in accordance with one embodiment of the present invention. In one embodiment of the present invention, the sample analysis module 310 may be configured to assert a quiet host signal prior to an RF reception by the receiver unit 300 to trigger the UI module processing unit 321 to reduce activity and enter a quiet mode and to suspend all activity by the communication module 330. Referring to FIG. 4, at step 410 when a quiet host signal is asserted by the sample analysis module processing unit 313, it is determined at step 420 whether the UI module processing unit 321 is in active processing mode. If it is determined that the UI module processing unit 321 is in active processing mode, then at step 430 the current cycle such as the current housekeeping cycle is performed, and the UI module processing unit 321 returned to the inactive mode at step 440, and the routine terminates. If the activity is user interface or communications related, then the brief pause while the quiet host signal is asserted will not be noticed by the user or affect communications.

On the other hand, referring back to FIG. 4, if at step 420 it is determined that the UI module processing unit 321 is not in an active mode, then at step 450, the UI module processing unit 321 is returned to the active mode, and at step 460 it is determined whether the UI module processing unit 321 is scheduled to execute some activity such as housekeeping during the reception of the data transmitted from the transmitter unit 102 (FIG. 1) by the analysis module 310. If at step 460 it is determined that the UI module processing unit 321 is not scheduled to be executing the housekeeping routine, then at step 470 the current active cycle is performed, and again, the UI module processing unit 321 is configured to enter the inactive mode at step 440 so as to maintain a quiet state during data reception by the analysis module 310.

Referring back to FIG. 4, at step 460 if it is determined that the UI module processing unit 321 is scheduled to execute some activity such as housekeeping during the reception of the data transmitted from the transmitter unit 102 (FIG. 1), then at step 480, the scheduled activity (e.g. housekeeping) is executed on an expedited basis, and at step 490 a time flag is generated which is associated with the expedited activity. The time flag in one embodiment is configured to modify the wakeup timer in the receiver unit 300 such that the UI module processing unit 321 may be configured to not wakeup during the RF transmission, again so as to maintain a quiet state during data reception by the analysis module 310.

In the manner described above, in accordance with the various embodiments of the present invention, there is provided a fault tolerant data receiver unit configured with a partitioned or separate processing units, each configured to perform a predetermined and/or specific processing associated with the one or more substantially non-overlapping functions of the data monitoring and management system. In one embodiment, the data receiver unit includes a communication module, a user interface module and a sample analysis module, and each module provided with a separate processing unit. In this manner, in one embodiment, each module is configured to perform predetermined functions associated with the data monitoring and management system to provide a modular, objected oriented processing architecture.

An analyte monitoring and management system in one embodiment of the present invention includes an analyte sensor, a transmitter unit coupled to the analyte sensor and configured to receive one or more analyte related signals from the analyte sensor, and a receiver unit configured to receive the one or more analyte related signals from the transmitter unit, the receiver unit including a sample analysis module and a user interface module operatively coupled to the sample analysis module.

The receiver unit may also further include a communication module operatively coupled to the user interface module, where the communication module may include a wired or a wireless communication module.

In one aspect, the wireless communication module may include one or more of a Bluetooth® communication module, a local area network data module, a wide area network data module, or an infrared communication module.

The analyte sensor may include a glucose sensor, where at least a portion of the analyte sensor is in fluid contact with an analyte of a patient.

The analyte may include one or more of an interstitial fluid, blood, or oxygen.

In one embodiment, the sample analysis module may be configured to receive one or more data associated with a respective one or more analyte samples for processing. Further, the one or more analyte samples are received from a respective one or more glucose test strips.

The sample analysis module may include a sample analysis module processing unit configured to process the one or more data associated with the respective one or more analyte samples, where the one or more analyte samples include blood glucose measurements.

In a further aspect, the sample analysis module processing unit may be further configured to process one or more analyte related signals from the transmitter unit.

In yet another aspect, the user interface module may include an output unit configured to display one or more signals associated with a condition of a patient.

The output unit may be configured to display one or more of a visual, auditory or vibratory output associated with the condition of the patient.

The visual output may include one or more of a directional arrow indicator, a color indicator, or a size indicator.

The auditory output may be configured to progressively increase or decrease the associated sound signal over a predetermined time period.

The vibratory output may be configured to progressively increase or decrease the associated vibratory signal over a predetermined time period.

In addition, the user interface module may include a user interface module processing unit operatively coupled to the output unit, where the user interface module processing unit may be configured to control the operation of the output unit.

In still another aspect, the user interface module may include an input unit configured to receive one or more input commands from a patient.

A data receiver unit in another embodiment of the present invention includes a first processing unit configured to perform a first predetermined processing, a second processing unit operatively coupled to the first processing unit, the second processing unit configured to perform a second predetermined processing, and a third processing unit operatively coupled to the second processing unit, the third processing unit configured to perform a third predetermined processing, where the first predetermined processing, the second predetermined processing and the third predetermined processing are substantially non-overlapping functions.

The receiver unit may also include a power supply unit operatively coupled to the second processing unit, the power supply unit configured to provide power to the first, second and third processing units.

In another aspect, the receiver unit may include a memory unit operatively coupled to the second processing unit, where the memory unit may include a non-volatile memory.

The memory unit may be configured to store one or more programming instructions for execution by one or more of the first processing unit, the second processing unit or the third processing unit.

A method in still another embodiment of the present invention includes configuring a first processing unit to perform a first predetermined processing, operatively coupling a second processing unit to the first processing unit, configuring the second processing unit to perform a second predetermined processing, operatively coupling a third processing unit to the second processing unit, and configuring the third processing unit to perform a third predetermined processing, where the first predetermined processing, the second predetermined processing and the third predetermined processing are substantially non-overlapping functions.

The method may also include operatively coupling a power supply to the second processing unit, and configuring the power supply unit to provide power to the first, second and the third processing units.

In another aspect, the method may also include further operatively coupling a memory unit to the second processing unit.

In yet another aspect, the method may also include configuring the memory unit to store one or more programming instructions for execution by one or more of the first processing unit, the second processing unit or the third processing unit.

The various processes described above including the processes performed by the UI module processing unit 321 and the sample analysis module 310 in the software application execution environment in the receiver unit 300 including the processes and routines described in conjunction with FIG. 4, may be embodied as computer programs developed using an object oriented language that allows the modeling of complex systems with modular objects to create abstractions that are representative of real world, physical objects and their interrelationships. The software required to carry out the inventive process, which may be stored in the memory unit 323 (for example) of the receiver unit 300 and may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method, comprising:
   receiving one or more analyte related signals;
   generating a quiet host signal prior to receiving the one or more analyte related signals; and
   in response to the generated quiet host signal, completing a current processing cycle, if any, and entering an inactive mode during the reception of the one or more analyte related signals.

2. The method of claim 1 wherein receiving the one or more analyte related signals includes wirelessly receiving the one or more analyte related signals.

3. The method of claim 1 including transcutaneously positioning at least a portion of an analyte sensor in fluid contact with interstitial fluid under skin layer.

4. The method of claim 3 wherein the analyte includes one or more of glucose, blood, or oxygen.

5. The method of claim 1 further including receiving data associated with an analyte sample.

6. The method of claim 5 wherein the analyte sample is received from a blood glucose test strip.

7. The method of claim 5 further including processing the data associated with the analyte sample.

8. The method of claim 5 wherein the analyte sample includes a blood glucose measurement.

9. The method of claim 1 further including outputting one or more signals associated with the condition of a patient including one or more of a directional arrow indicator, a color indicator, or a monitored condition level indicator.

10. The method of claim 9 wherein outputting the one or more signals associated with the condition of the patient includes progressively increasing or decreasing an associated outputted signal over a predetermined time period.

11. A method, comprising:
    performing, using a first processing unit, a first predetermined routine including generating a predetermined signal;
    performing, using a second processing unit, a second predetermined routine including completing a first processing cycle and subsequently entering an inactive mode if the predetermined signal is received during a first processing cycle, or entering an active mode and determining whether a second processing cycle is to be performed during a data reception period if the predetermined signal is received other than during the first processing cycle.

12. The method of claim 11, wherein the second predetermined routine further includes:
    expediting the second processing cycle, generating a time flag associated with the expedited second processing cycle, and entering the inactive mode if it is determined that the first processing cycle is to be performed during the data reception period; and performing the second processing cycle and subsequently entering the inactive mode if it is determined that the first processing cycle is to be performed during the data reception period.

13. The method of claim 12, further including providing the generated time flag and maintaining the second processing unit in the inactive mode during the data reception period.

14. The method of claim 11, further comprising performing, using a third processing unit, a third predetermined routine.

15. The method of claim 11, wherein the second processing cycle includes a housekeeping routine.

16. A method, comprising:

receiving one or more analyte related signals from an analyte sensor;

performing, using a first processing unit, a first predetermined processing routine, and performing, using a second processing unit, a second predetermined processing routine, wherein the first and second predetermined processing routines are non-overlapping; and receiving data from electronics coupled to the analyte sensor during a data reception cycle and, prior to the data reception cycle, generating a quiet host signal and, in response to the quiet host signal, placing one of the first or the second processing units in an inactive mode, wherein the inactive mode includes suspending all activity of the another one of the first or second processing units.

17. The method of claim 16, wherein receiving the one or more analyte related signals includes wirelessly receiving the one or more analyte related signals from electronics operatively coupled to the analyte sensor.

18. The method of claim 16, further comprising providing medication information based on the received one or more analyte related signals for administration to a subject.

19. The method of claim 18, wherein the medication information includes an insulin amount.

* * * * *